(12) United States Patent
Barreiro Flores

(10) Patent No.: US 8,697,712 B2
(45) Date of Patent: Apr. 15, 2014

(54) PRESENTATION OF AN ANTIVIRAL PHARMACEUTICAL COMPOSITION

(75) Inventor: Francisco Barreiro Flores, Cuajimalpa (MX)

(73) Assignee: Laboratorios Liomont, S.A. DE C.V., Cuajimalpa (MX)

( * ) Notice: Subject to any disclaimer, the term of this patent is extended or adjusted under 35 U.S.C. 154(b) by 1417 days.

(21) Appl. No.: 11/547,275

(22) PCT Filed: Apr. 5, 2004

(86) PCT No.: PCT/MX2004/000025
§ 371 (c)(1),
(2), (4) Date: Feb. 6, 2007

(87) PCT Pub. No.: WO2005/099713
PCT Pub. Date: Oct. 27, 2005

(65) Prior Publication Data
US 2008/0287470 A1    Nov. 20, 2008

(51) Int. Cl.
*A61K 31/522* (2006.01)
*A61K 51/12* (2006.01)
*A61K 47/00* (2006.01)

(52) U.S. Cl.
CPC ............. *A61K 31/522* (2013.01); *A61K 51/121* (2013.01); *A61K 47/00* (2013.01)
USPC .................................. 514/263.31

(58) Field of Classification Search
CPC ..... A61K 31/522; A61K 47/02; A61K 47/10; A61K 47/20
USPC ................................... 514/263.31
See application file for complete search history.

(56) References Cited

U.S. PATENT DOCUMENTS

| 5,331,012 | A | * | 7/1994 | Riddick et al. ................. 514/626 |
| 5,585,379 | A | * | 12/1996 | Sintov et al. ............. 514/263.38 |
| 6,379,692 | B1 | | 4/2002 | Rao et al. |
| 2005/0031655 | A1 | * | 2/2005 | Karpov ......................... 424/401 |

FOREIGN PATENT DOCUMENTS

WO    WO00/15193    *  3/2000

OTHER PUBLICATIONS

Ansel et al., Pharmaceutical Dosage Forms and Drug Delivery Systems, 5th Ed. 1990, p. 201-202.*
Ansel et al., Pharmaceutical Dosage Forms and Drug Delivery Systems, 5th Ed. 1990, p. 104-107.*
Ansel et al. (Pharmaceutical Dosage Forms and Drug Delivery Systems, 5th Ed. 1990, p. 94-99).*

* cited by examiner

*Primary Examiner* — Bong-Sook Baek
(74) *Attorney, Agent, or Firm* — Birch, Stewart, Kolasch & Birch LLP

(57) ABSTRACT

A new presentation of an antiviral pharmaceutical composition in solution form comprising as an active agent, aciclovir in an amount of about 5% by weight; a solvent in an amount of from about 10 to 20% by weight; a solubilizing agent in an amount of from about 1.5 to 5.0% by weight; a humectant agent in an amount of from about 2 to 10% by weight; an anti-itching agent in an amount of from about 0.05 to 1.0% by weight; an antioxidant agent in an amount of from about 0.1 to 0.5% by weight and demineralized water in an amount of from about 20 to 80% by weight.

6 Claims, No Drawings

PRESENTATION OF AN ANTIVIRAL PHARMACEUTICAL COMPOSITION

This invention relates to a topical pharmaceutical formulation, useful in the treatment of skin viral infections and particularly to a pharmaceutical composition containing as an active agent 9-(2-hydroxyethoxymethyl)guanine, also known as acyclovir, for the treatment of herpes.

It has been common up to now to prepare a drug containing as an active agent aciclovir for the treatment of herpes, in the form of an ointment, cream, or salve, and until now no presentation of this drug as a solution has been made.

Aciclovir, due to its physical properties, exhibits low water solubility, and is almost wholly insoluble in a hydrophobic solvent system; therefore, a topical formulation cannot be produced easily containing enough dissolved concentration of the active agent; whereby the activity of said agent is not properly usable for the intended purpose.

It is the main object of this invention the formulation of a pharmaceutical product containing as an active agent aciclovir, that is stable for long periods of time without losing the pharmaceutical activity thereof, while avoiding, as long as possible, the skin irritation in a patient to whom it is applied.

It is another object of this invention to provide a pharmaceutical composition useful in the treatment of herpes, in the form of a solution with atomizer, to avoid the application thereof by rubbing, thus preventing a possible infection and additional irritation of the zone to be treated.

Another further object of the invention is the formulation of a drug containing as an active agent aciclovir in the form of a solution with atomizer, stable and easy to apply.

According to the teachings of the invention, the pharmaceutical composition forming the subject matter of this application, in the form of a solution, exhibits stable characteristics and a curative effectiveness suitable for the application thereof on the affected area of a patient.

Accordingly, this invention provides a pharmaceutical formulation in solution form with atomizer for topical application of aciclovir, comprising:
a) the compound 9-(2-hydroxyethoxymethyl)guanine, as an active agent;
b) solvents,
c) solubilizers,
d) humectants,
e) anti-itching agents
f) anti-oxidant agents; and
g) demineralized water.

The topical formulation object of this application contains the active agent aciclovir, as an anti-herpes agent, of the formula:

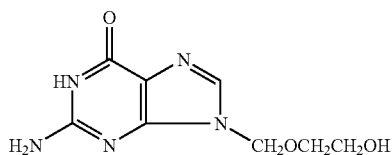

in an amount of about 5% by weight; from about 10 to 20% by weight of a pharmaceutically acceptable solvent; a solubilizing agent in an amount of from about 1.5 to 5.0% by weight; a humectant agent in a ratio of from 2 to 10% by weight; an anti-itching agent in an amount of from about 0.05 to 1.0% by weight, an antioxidant agent in an amount of from about 0.1 to 0.5% by weight; with the rest being demineralized water.

It is to be understood that all of the ingredients constituting the pharmaceutical composition object of this application must be "pharmaceutically acceptable ingredients", in the sense that they must be compatible with other ingredients of the formulation and must be innocuous for the patient.

The solvents suitable for the formulation of this invention are selected from the group consisting of butyl alcohol, corn oil, cottonseed oil, ethyl alcohol, isopropyl alcohol, polyethylene glycol, propylene glycol, glycerin, benzyl benzoate and/or water; the solubilizing agent is selected from the group consisting of ammonium carbonate, diethanol amine, potassium hydroxide, sodium hydroxide, sodium bicarbonate, sodium borate, sodium carbonate, monoethanol amine, amino methyl propanol, triethanol amine and sorbitan derivatives; the preferred humectant agents being selected from the group consisting of glycerin, sorbitol, propylene glycol and/or mineral oil; the preferred anti-itching agent being selected from the group consisting of methanol and/or camphor; the useful antioxidants in the formulation of the pharmaceutical composition of this invention are those comprised in the group consisting of ascorbic acid, butylated hydroxyanisole, hypophosphorous acid, potassium metabisulfite, sodium metabisulfite, sodium thiosulfate, tocopherol and/or propyl galate.

The preferred solvent to be used in this invention is selected from ethyl alcohol and/or isopropyl alcohol; the preferred solubilizers, to be used are selected from sodium hydroxide and/or amino methyl propanol; the preferred humectant agent is polypropylene glycol and the preferred anti-itching agent is camphor, while the preferred antioxidant is sodium metabisulfite. All of the ingredients or constituent agents in the pharmaceutical composition of this invention are as employed in the hereinabove mentioned amounts.

The pharmaceutical composition of this invention is useful in the treatment or prophylaxis of infectious diseases caused by herpes simplex virus and zoster virus in human beings; in the form of a solution with atomizer, whereby the drug can be applied as a spray, thus avoiding the application of said drug by rubbing the same onto the skin, and thus preventing an additional infection source in the infected zone to be treated.

The new pharmaceutical presentation of the present application can include also some other ingredients adding suitable characteristics for the use of the product, such as, for instance, an anesthetic agent; and it will also be obvious that it could be admixed or combined with another given antiviral agent in order to improve the effectiveness of the use of said pharmaceutical composition, without departing from the spirit of the invention which, as can be deducted, is to provide an antiviral pharmaceutical composition in the form of a solution, applicable as a spray by means of an atomizer device.

The invention claimed is:
1. An atomizer for topical administration of aciclovir, wherein said atomizer comprises an antiviral pharmaceutical composition in the form of a solution, said pharmaceutical composition comprising:
as an active agent aciclovir in an amount of 5% by weight;
a solvent in an amount of from 10 to 20% by weight, wherein said solvent is ethyl alcohol and/or isopropyl alcohol;
a solubilizing agent in an amount of from 1.5 to 5.0% by weight, wherein said solubilizing agent is selected from the group consisting of sodium carbonate, diethanol amine, potassium hydroxide, sodium hydroxide, sodium bicarbonate, sodium borate, sodium carbonate, monoethanol amine, amino methyl propanol, triethanol amine and/or sorbitan derivatives;

a humectant agent in an amount of from 2 to 10% by weight, wherein said humectant agent is selected from the group consisting of glycerin, sorbitol, polypropylene glycol and/or mineral oil;

an anti-itching agent of ethanol and/or camphor in an amount of from 0.05 to 1.0% by weight;

an antioxidant agent in an amount of from 0.1 to 0.5% by weight, wherein said antioxidant agent is selected from the group consisting of ascorbic acid, butylated hydroxyanisol, hypophosphorous acid, potassium metabisulfite, sodium metabisulfite, sodium thiosulfate, tocopherol and/or propyl galate; and purified water in an amount of from 20 to 80% by weight.

2. The atomizer comprising the pharmaceutical composition in the form of a solution according to claim 1, wherein said solvent is ethyl alcohol and/or isopropyl alcohol.

3. The atomizer comprising the pharmaceutical composition in the form of a solution according to claim 1, wherein said solubilizing agent is sodium hydroxide and/or amino methyl propanol.

4. The atomizer comprising the pharmaceutical composition in the form of a solution according to claim 1, wherein said humectant agent is polypropylene glycol.

5. The atomizer comprising the pharmaceutical composition in the form of a solution according to claim 1, wherein said anti-itching agent is camphor.

6. The atomizer comprising the pharmaceutical composition in the form of a solution according to claim 1, wherein said antioxidant agent is sodium metabisulfite.

\* \* \* \* \*